(12) United States Patent
Obradovic

(10) Patent No.: US 10,538,471 B2
(45) Date of Patent: Jan. 21, 2020

(54) MANUFACTURE OF BISPHENOL A

(71) Applicant: SABIC GLOBAL TECHNOLOGIES B.V., Bergen op Zoom (NL)

(72) Inventor: Branislav Obradovic, Bergen op Zoom (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/317,325

(22) PCT Filed: Jul. 20, 2017

(86) PCT No.: PCT/IB2017/054409
§ 371 (c)(1),
(2) Date: Jan. 11, 2019

(87) PCT Pub. No.: WO2018/015923
PCT Pub. Date: Jan. 25, 2018

(65) Prior Publication Data
US 2019/0315670 A1    Oct. 17, 2019

(30) Foreign Application Priority Data

Jul. 22, 2016  (EP) .................................... 16180769
Jan. 12, 2017  (EP) .................................... 17151147

(51) Int. Cl.
*C07C 39/16*  (2006.01)
*C07C 37/20*  (2006.01)
*C07C 37/84*  (2006.01)

(52) U.S. Cl.
CPC .............. *C07C 37/20* (2013.01); *C07C 37/84* (2013.01); *C07C 39/16* (2013.01); *C07B 2200/13* (2013.01)

(58) Field of Classification Search
CPC .......... C07C 39/16; C07C 37/20; C07C 37/84
See application file for complete search history.

(56) References Cited

U.S. PATENT DOCUMENTS

| 7,067,704 B2 | 6/2006 | Young et al. |
| 7,989,666 B2 | 8/2011 | Hong et al. |
| 2005/0176918 A1 | 8/2005 | Neumann et al. |

FOREIGN PATENT DOCUMENTS

| CN | 101525275 A | 9/2009 |
| EP | 1669339 A1 | 6/2006 |
| JP | H05345737 A | 12/1993 |
| WO | 9419302 A1 | 9/1994 |
| WO | 0240435 A1 | 5/2002 |
| WO | 0249435 A1 | 6/2002 |

OTHER PUBLICATIONS

European Search Report for EP16180769, Filing Date Jul. 22, 2016, Date of Completion of Search Dec. 22, 2016, 2 pages.
International Search Report; International Application No. PCT/IB2017/054409; International Filing Date: Jul. 20, 2017; dated Nov. 3, 2017; 6 pages.
Written Opinion; International Application No. PCT/IB2017/054409; International Filing Date: Jul. 20, 2017; dated Nov. 3, 2017; 5 pages.

*Primary Examiner* — Ana Z Muresan
(74) *Attorney, Agent, or Firm* — Cantor Colburn LLP

(57) ABSTRACT

The invention is directed to a method for the manufacture of bisphenol A, and to bisphenol A/phenol adduct crystals. The method of the invention comprises: a) reacting phenol and acetone in the presence of an acidic catalyst to form a reaction product comprising an initial concentration of bisphenol A and an initial concentration of impurities; b) diluting the reaction product with phenol, water and/or acetone, so as to decrease the impurity concentration to 50% by weight or less of the initial concentration of impurities, and adding bisphenol A to increase the concentration thereof in the reaction product; and thereafter c) crystallising a bisphenol A/phenol adduct from the reaction product to produce a crystallised bisphenol A product.

18 Claims, 1 Drawing Sheet

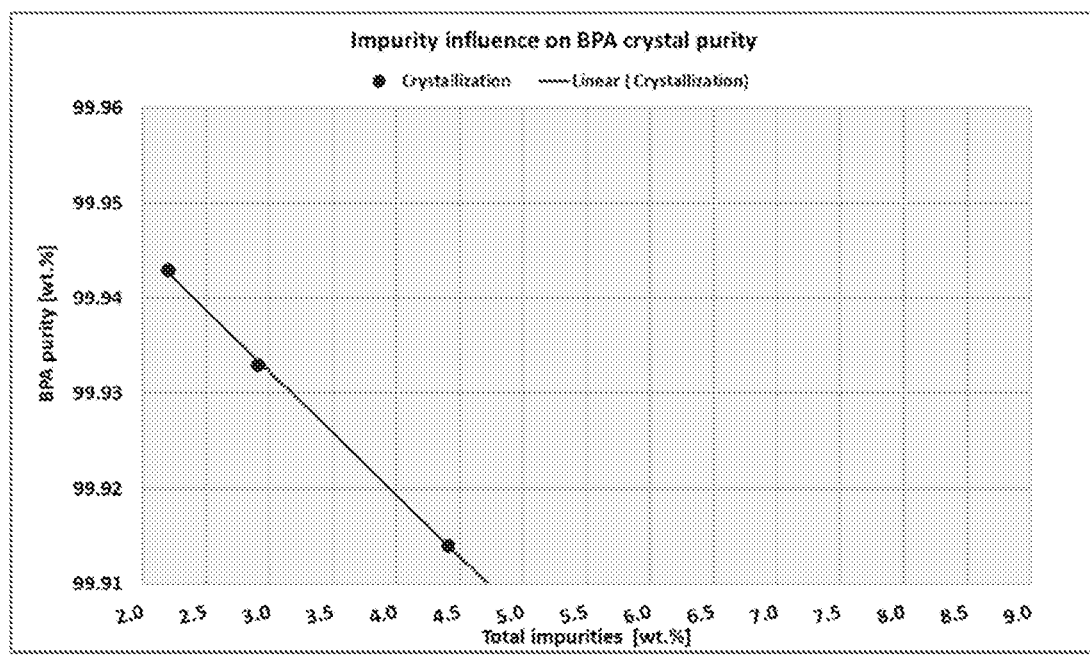

MANUFACTURE OF BISPHENOL A

CROSS REFERENCE TO RELATED APPLICATIONS

This application is a 371 of International Application No. PCT/M2017/054409, filed Jul. 20, 2017, which claims priority to EP 16180769.8, filed Jul. 22, 2016, and EP 17151147.0, filed Jan. 12, 2017, which are incorporated herein by reference in their entirety.

The invention is directed to a method for the manufacture of bisphenol A, and to bisphenol A/phenol adduct crystals.

Bisphenol A (2,2'-bis(4-hydroxyphenyl)propane, also known as p,p-BPA) is predominantly used as an intermediate for the production of other products. The main uses of bisphenol A are binding, plasticising, and hardening functions in plastic products, paints/lacquers, binding materials and filler materials. The primary use for bisphenol A is in the production of polycarbonate resins, epoxy resins, unsaturated polyester, polysulphone, polyetherimide and polyarylate resins.

Bisphenol A is commercially prepared by condensing two moles of phenol with a mole of acetone in the presence of an acid catalyst as shown in equation (1) below.

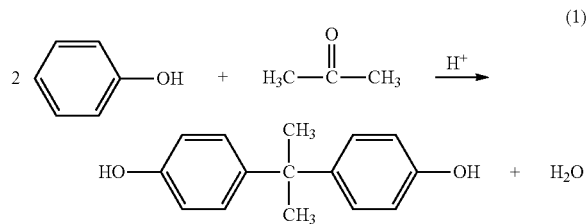

The phenol is present in the reaction in a molar excess of the stoichiometric requirement. During the condensation, a number of by-products are formed such as dimers and isomeric forms of the bisphenol A. These are considered contaminants of the desired product. The main contaminants present are the 2,4'-bisphenol isomer (2-(2-hydroxyphenyl)-2-(4-hydroxyphenyl)propane also known as o,p-bisphenol A), 2,4-bis($\alpha,\alpha$-dimethyl-4-hydroxybenzyl)phenol also known as BPX-1, 4-(2-(4-(4-hydroxyphenyl)-2,2,4-trimethylchroman-6-yl)propan-2-yl)phenol also known as BPX-2, 4-(4'-hydroxyphenyl)-2,2,4-trimethylchroman also known as codimer or Dianin's compound, and 2-(4'-hydroxyphenyl)-2,4,4-trimethylchroman also known as isomeric codimer or an isomer of Dianin's compound. These contaminants are carried in the product stream from the condensation reaction zone, with water, unreacted phenol and unreacted acetone. When bisphenol A is used for preparing polycarbonate polymer, it is however required that the bisphenol A is very pure, because these contaminants have the tendency to form colour bodies under the alkaline reaction conditions used in polycarbonate production. In particular for so-called melt polycarbonate, which is polycarbonate made in a process where bisphenol A and a second reactant (diphenyl carbonate) are reacted in melt phase, it is important the bisphenol A used is very pure. Currently, the purification of the desired product bisphenol A is a costly and multi-step procedure.

Commercial processes for purifying bisphenol A out of the reaction mixture of p,p-BPA with its various isomers and by-products use crystallisation as key process step. The mixture can be untreated reactor effluent, in which case excess phenol is present that acts as solvent, or the reaction effluent may be treated to remove excess water, acetone and phenol, in which case the mixture is concentrated in phenol or even phenol free. In the crystallisation step, the reaction mixture is cooled to form a slurry containing a crystalline bisphenol A/phenol adduct. In case of a concentrated or phenol free reaction mixture, the mixture can be dissolved (or diluted) in a solvent at elevated temperature (solvents can be various aromatic, chlorinated alkanes, or simple alkanes) before cooling down the solution. Due to the cooling process, possibly combined by solvent removal to increase the concentration, crystals are created that have a high concentration of the desired isomer, being the p,p-BPA isomer. The slurry is then filtered to remove the excess liquid and washed with clean solvent to obtain a cake (crystal mass) that is as free as possible of the liquid phase.

These commercial processes all have the disadvantage that the crystal is still contaminated to a large extent. In order to obtain high purity p,p-BPA of more than 99.90% purity, commercial processes either use a two step crystallisation approach which consists of two identical single adduct crystallisation stages, or process wherein single adduct crystallisation is followed by melt crystallisation. Examples of these processes are, for instance, described in WO-A-02/40435, EP-A-0 718 268, EP-A-1 367 043, EP-A-1 728 777, U.S. Pat. Nos. 5,648,561, and 5,371,302. Both these processes require significant investment and operational costs as they involve a two stage bisphenol A purification process.

WO 94/19302 discloses a process for the production of high purity and ultrapure bisphenol-A in which 4-12 mol phenol is reacted with 1 mol acetone in a multistage suspended bed reactor column.

EP1669339 discloses a method for preparing bisphenol A, comprising the steps of transferring phenol and acetone into a reaction zone charged with condensation catalyst, obtaining a stream containing bisphenol A after reaction; transferring the obtained stream containing bisphenol A into a rectification zone, obtaining a product fraction primarily containing bisphenol A and phenol; and transferring the product fraction primarily containing bisphenol A and phenol into a crystallization zone to obtain a bisphenol A product; wherein a water-depleted fraction primarily containing phenol, bisphenol A and acetone is obtained from the rectification zone, and said water-depleted fraction is cooled and returned as a cycled stream to the reaction zone.

There remains a need in the art for the production of highly pure bisphenol A in a relatively simple and cost-effective manner, and in particular for the production of highly pure bisphenol A in a single stage operation.

Objective of the invention is to overcome at least part of the disadvantages faced in the prior art.

BRIEF SUMMARY

The inventors found that this objective can, at least in part, be met by adding specific compounds to the reaction product before crystallising.

Accordingly, in a first aspect the invention is directed to a method for the manufacture of bisphenol A comprising:
  a) reacting phenol and acetone in the presence of an acidic catalyst to form a reaction product comprising an initial concentration of bisphenol A and an initial concentration of impurities;
  b) diluting the reaction product with phenol, water and/or acetone, so as to decrease the impurity concentration to 50% or less of the initial concentration of impurities, and adding bisphenol A to increase the concentration thereof in the reaction product; and thereafter c) crystallising a bisphenol A/phenol adduct from the reaction product to produce a crystallised bisphenol A product.

BRIEF DESCRIPTION OF THE DRAWINGS

FIG. 1 is a graphical illustration of the total impurity versus achieved bisphenol A purity of the examples.

DETAILED DESCRIPTION

The inventors surprisingly found that reducing the content of impurities vis-à-vis the content of bisphenol A in the crystalliser feed results in highly pure bisphenol A/phenol adduct crystals, that can be obtained in a single crystallisation step.

The first step of reacting phenol and acetone in the presence of an acidic catalyst to form a reaction product comprising an initial concentration of bisphenol A and an initial concentration of impurities is commonly known in the art.

The molar ratio of phenol to acetone is usually in the range of 3-30 moles of phenol per mole of acetone, and preferably 5-15 moles of phenol per mole of acetone. If the molar ratio is smaller than 3 moles of phenol per mole of acetone, then the reaction speed is likely to be too slow. If it molar ratio is larger than 30 moles of phenol per mole of acetone then the System becomes too dilute to have commercial significance.

The reaction temperature can be 40-150° C., preferably 60-110° C., more preferably 50-100° C. If the reaction temperature is lower than 40° C., not only the reaction speed is slow but also the reaction solution has a very high viscosity and may solidify. On the other hand, if the reaction temperature exceeds 150° C., it becomes difficult to control the reaction, and a selectivity of bisphenol A (p,p-BPA) is lowered. In addition, the catalyst may be decomposed or deteriorated.

The acidic catalyst can be a homogeneous acidic catalyst or a solid acidic catalyst. In view of low corrosiveness of devices and easiness in separating the catalyst from the reaction mixture, solid acidic catalysts are preferred.

When a homogenous acidic catalyst is used, hydrochloric acid, sulphuric acid and the like are generally used. Sulphuric acid is preferably used since it can be easily separated. When a solid acidic catalyst is used, a sulphonic acid-type ion-exchange resin is generally used. Examples thereof include sulphonated styrene-divinylbenzene copolymers, sulphonated cross-linked styrene polymers, phenol formaldehyde-sulphonic acid resins, and benzene formaldehyde-sulphonic acid resins. These catalysts may be used individually or in combination.

The reaction of step a) may be performed batch-wise or continuously. Preferably, the reaction is performed in a fixed bed continuous reactor in which phenol and acetone are continuously fed into a reactor filled with an acid-type ion-exchange resin to react them. The reactor may be a single reactor, or may be two or more reactors that are connected in series.

Optionally, the reaction mixture of step a) is subjected to a step for removing unreacted acetone, and water, e.g. by distillation. Such optional distillation may be performed under reduced pressure using a distillation column. In general such distillation is carried out at a pressure of 6.5-80 kPa and at a temperature of 70-180° C. Unreacted phenol then boils by azeotropy, and part thereof is removed.

Optionally, the bisphenol A may be concentrated by further removal of phenol. Such further distillation may typically be performed at 100-170° C. and a pressure of 5-70 kPa.

The reaction product obtained in step a) usually includes, in addition to bisphenol A, unreacted acetone, unreacted phenol, water produced during the reaction and other by-products. The reaction product typically comprises 10-50% by total weight of the reaction product of bisphenol A, preferably 15-40%;

60-85% by total weight of the reaction product of phenol, preferably 65-80%;

0-5% by total weight of the reaction product of water, preferably 0-3%;

0-3% by total weight of the reaction product of acetone, preferably 0-1.5%; and 0-20% by total weight of the reaction product of by-products, typically 2-16%.

When the concentration of bisphenol A is less than 10% by total weight of the reaction product, the recovery rate of adduct crystals becomes low. When the concentration of bisphenol A is more than 50% by total weight of the reaction product, the viscosity of the slurry becomes high, so that the transportation of the slurry becomes difficult.

In step b) of the method, the reaction product obtained in step a) is diluted with phenol, water and/or acetone. Preferably, the dilution is achieved with addition of at least phenol, optionally supplemented with water and/or acetone. As a result of the dilution, the impurity concentration is decreased to 50% or less of the initial concentration of impurities. It is of course also possible to further dilute the reaction product, such as to achieve an impurity concentration of 45% or less of the initial concentration of impurities, such as 40% or less, or 20-35%.

The initial concentration of impurities can be 5-15% by total weight of the reaction product, such as 6-12% by total weight of the phenol free reaction product or less, or 7-10% by total weight of the phenol free reaction product.

The impurities that may be present in the reaction product obtained in step a) may include one or more selected from the group consisting of o,p-bisphenol A (2-(2-hydroxyphenyl)-2-(4-hydroxyphenyl)propane), BPX-1 (2,4-bis(α,α-dimethyl-4-hydroxybenzyl)phenol), Chr-1 (4'-hydroxyphenyl-2,2,4-trimethyl chroman, also known as chroman-1), Spi (2,2',3,3'-tetrahydro-1,1'-spirobi[indene], also known as spirobiindan), BPX-2 (4-(2-(4-(4-hydroxyphenyl)-2,2,4-trimethylchroman-6-yl)propan-2-yl)phenol), DMX (9,9-dimethylxanthene), 4-(4"-hydroxyphenyl)-2,2,4-trimethylchroman, and 2-(4'-hydroxyphenyl)-2,4,4-trimethylchroman. The impurities that may be present in the reaction product obtained in step a) may include o,p-bisphenol A. The impurities that may be present in the reaction product obtained in step a) may include one or more of (2-(2-hydroxyphenyl)-2-(4-hydroxyphenyl)propane) BPX-1, BPX-2, and DMX.

Step b) of the method further comprises adding bisphenol A to increase the concentration thereof in the reaction product. The bisphenol A can be a commercial grade bisphenol A. It is not required that the bisphenol A has specifically high purity grade. However, it is also possible to add highly pure bisphenol A as manufactured according to the method of the invention via a recycle.

Although the bisphenol A may be added prior to diluting the reaction product obtained in step a), it is preferred that the bisphenol A is added after diluting the reaction product obtained in step a). The addition of bisphenol A in step b) is preferably such that the concentration of bisphenol A in the product is set to 70-200% of the initial concentration of bisphenol A, preferably 75-150%, more preferably 80-125%, and most preferably, 90-110%. For example, the concentration of bisphenol A in the mixture after step b) can be more or less the same as the initial concentration of bisphenol A. In terms of weight percentages, the concentration of bisphenol A after step b) may, for instance, be in the range of 15-40% by total weight of the mixture after step b), such as 18-35%, or 20-30%.

Preferably, the weight ratio of phenol to bisphenol A in the reaction product prior to step b) is 70-200% of the weight ratio of phenol to bisphenol A in the reaction product after step b), more preferably 75-150%, even more preferably 80-125%, and most preferably 90-110%.

The concentration of p,p-bisphenol A in the mixture after step b) (i.e. the crystallisation feed) can be 18-32% by total weight of the diluted reaction product by adding bisphenol A, such as 20-30%, or 22-28%.

Step b) of the method may further comprise adding acetone to increase the concentration of acetone in the mixture. Preferably, the weight ratio of acetone to bisphenol A in the reaction product prior to step b) is 70-200% of the weight ratio of acetone to bisphenol A in the reaction product after step b), more preferably 75-150%, even more preferably 80-125%, and most preferably 90-110%.

Step b) of the method may further comprise (either individually or in combination with the above mentioned addition of acetone) adding water to increase the concentration of water in the mixture. Preferably, the weight ratio of water to bisphenol A in the reaction product prior to step b) is 70-200% of the weight ratio of water to bisphenol A in the reaction product after step b), more preferably 75-150%, even more preferably 80-125%, and most preferably 90-110%.

The crystallisation may be performed in a conventional manner by controlled cooling. Preferably, crystallisation is performed in a single step, thereby reducing operations costs. The invention surprisingly allows a one step crystallisation, due to the decreased level of impurities in the product mixture after step b). Single step crystallisation is preferred over multiple step crystallisation, although multiple step crystallisation is also possible, wherein the crystallisation comprises two or more steps in series.

The crystallising step can suitably be carried out at a temperature in the range of 40-70° C., preferably in the range of 45-65° C., more preferably in the range of 50-60° C.

Typically, the mixture is cooled to a temperature of 40-70° C. so as to crystallise the bisphenol A/phenol adduct to prepare a slurry. Typically, the pure bisphenol A/phenol adduct that forms during the crystallisation can have a molar composition of about 1:1. On a weight basis the composition may typically comprise about 70.8% by total weight of the bisphenol A/phenol adduct of bisphenol A and about 29.2% by total weight of the bisphenol A/phenol adduct of phenol. The cooling may, for instance, be carried out by means of an external heat exchanger or by a vacuum cooling crystallisation method in which the mixture is cooled down by adding water thereto to make use of vaporisation latent heat of water under reduced pressure. A relatively high crystallisation temperature can result in higher purity, but the crystal yield will be lower. A relatively low crystallisation temperature can provide desirable yield but with lower purity. Preferably, the crystallisation temperature is in the range of 50-60° C.

Cooling may be performed in multiple subsequent cooling stages in order to achieve even higher purity. For example, a first cooling stage may be followed by a dwell time, after which a second cooling stage may be performed with an optional subsequent second dwell time and an optional subsequent third cooling stage.

The cooling may represent (or each of the cooling stages may independently represent) a cooling of the mixture with 5-40° C., such as 10-35° C., or 15-20° C., using a cooling rate of 0.1-1° C./min, such as 0.02-0.5° C./min. Each of the dwell times can last 20-120 minutes, such as 30-90 minutes. A smaller cooling rate can result in a higher purity product, but takes more time. Similarly, a longer dwell time can result in higher purity but takes more time.

After crystallisation, the bisphenol A adduct product comprises 99.8% or more by total weight of p,p-bisphenol A on phenol free basis, preferably 99.9% or more, more preferably 99.92% or more on phenol free basis.

Next, the slurry containing the bisphenol A/phenol adduct crystals can be separated into the bisphenol A/phenol adduct and the crystallisation mother liquid containing reaction by-products by conventional means such as filtering and centrifugal separation. A part of the crystallisation mother liquid may be recycled in the reactor or to the crystallisation raw material. To obtain the bisphenol A product without any phenol, e.g. for the production of polycarbonate or epoxy resins, the phenol is removed by first melting the adduct and then stripping the phenol out of the molten mixture. The bisphenol A is then solidified, e.g. in a flaking or prilling unit.

Optionally, the obtained crystals may be subjected to washing, such as with liquid phenol. After filtration, the crystals can be obtained.

In an embodiment, part of the bisphenol A product is recycled and used in step b) of the method for increasing the concentration thereof in the reaction product.

The bisphenol A/phenol adduct crystals that can be obtained with the method of the invention are surprisingly pure. Therefore, the invention is further directed to bisphenol A/phenol adduct crystals obtainable by the method of the invention, wherein said bisphenol A has a purity of at least 99.90% on a phenol free basis. Preferably, these adduct crystals have been obtained using a single step crystallisation. Hitherto it was not possible to obtain such pure bisphenol A/phenol adduct crystals using only a single crystallisation step.

All references cited herein are hereby completely incorporated by reference to the same extent as if each reference were individually and specifically indicated to be incorporated by reference and were set forth in its entirety herein. EP 16180769.8 filed Jul. 22, 2016 and EP 17151147.0 filed Jan. 12, 2017 are both incorporated herein in their entirety.

The use of the terms "a" and "an" and "the" and similar referents in the context of describing the invention (especially in the context of the claims) are to be construed to cover both the singular and the plural, unless otherwise indicated herein or clearly contradicted by context. The terms "comprising", "having", "including" and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. For the purpose of the description and of the appended claims, except where otherwise indicated, all numbers expressing amounts, quantities, percentages, and so forth, are to be understood as being modified in all instances by the term "about". Also, all ranges include any combination of the maximum and minimum points disclosed and include and intermediate ranges therein, which may or may not be specifically enumerated herein.

Preferred embodiments of this invention are described herein. Variation of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject-matter recited in the claims appended hereto as permitted by applicable law. Moreover, any combination of the above-described elements in all possible variations thereof is encompassed by the invention unless otherwise indicated herein or otherwise clearly contradicted by context. The claims are to be construed to include alternative embodiments to the extent permitted by the prior art.

For the purpose of clarity and a concise description features are described herein as part of the same or separate embodiments, however, it will be appreciated that the scope of the invention may include embodiments having combinations of all or some of the features described.

The invention will now be further illustrated by the following non-limiting examples.

EXAMPLES

Experimental work was done using a Lab Max™ system coupled with two probe based instruments: FBRM (Focused Beam Reflectance Measurement) and PVM (Particle Video Microscope) all supplied by Mettler Toledo™. The Lab Max™ system is further coupled with a lab scale pressure filter unit. The Lab Max is a fully automated, lab crystallisation temperature control unit. The system consists of lab crystalliser with PVM and FBRM probe, Lab Max™ temperature controller, and filter unit.

FBRM is a laser based instrument. The probe is attached on the top of the crystalliser and reaches into the crystallising solution. Inside the probe is a laser light source. The laser light is sent through a rotational optic lens at the tip of the probe. In this way the laser beam scans through the solution in a circular motion. The linear velocity of the circulation is set to 2 m/s, and it can be adjusted. Once the beam crosses through the solid particle (or any other object, or example a bubble, which has different refractive index) the laser light is back scattered, and received by the sensors in the probe. In this way the probe is able to detect chord lengths of the crystals through which the beam scans.

The PVM is the second probe instrument, and it is also attached on the top of the crystalliser in similar fashion as FBRM. This probe also reaches into the solution, and it is capable of taking real time photos. The photos are of the dimensions of 800 with 1000 micrometers.

Each of the FBRM, the Lab Max and the PVM are connected to a personal computer.

The lab crystalliser is a 2 litre jacketed glass vessel equipped with a pitched blade turbine stirrer. The temperature of the crystalliser is controlled by the Lab Max™ via heating oil. Lab Max™ temperature control can be programmed to follow different cooling or heating rates (° C./min), or different cooling or heating curves (second, third order curve, exponential curve, etc.). The stirrer speed is also controlled by the Lab Max™. Filtration and washing of the cake are performed in the lab pressure filter. The filtration and washing temperature is kept the same as the crystallisation end-temperature with a water bath. This way the crystals are not going to dissolve or grow during the filtration and washing. The composition of the obtained crystals is determined by HPLC (high performance liquid chromatography) analysis. The system is equipped with an automated dosing unit. This unit is used to add water or another chemical in different experiments.

The compositions of the batched used in the experiments are shown in Table 1. In order to achieve lower levels of total impurities in crystallisation, the reaction effluent was diluted with pure phenol, and then Mitsui bisphenol A (99.96 wt. % purity) was added to bring the bisphenol A concentration to ~25 wt. %. The same was done with water and acetone. The net effect was a crystallisation solution which had the same content of p,p-BPA, water and acetone as the original reactor effluent, but lower total impurity content. The detailed compositions of the diluted crystallisation solutions are given in table 2.

All crystallisation experiments were performed following the same crystallisation cooling protocol. The main purpose of the protocol is to have repeatable and reproducible results. The five distinct steps in the cooling profile are:

1. Bringing the Sample to Initial Temperature.

Each experiment uses 350-400 grams of crystallisation solution. The reactor effluent is heated up in a water bath for 1-2 hours to 75-80° C. During this heating, part of the sample which is in a solid (crystals) state will dissolve. When there are no more crystals in the sample, the sample is placed in the crystalliser vessel.

2. Preparation of the Desired Solution.

The desired decreased level of the total impurities is achieved by adding the calculated amount of phenol to reactor effluent in order to decrease the impurity content. Then, the calculated amount of pure bisphenol A and water is added to bring their levels approximately to the original values. After finishing the sample preparation in the crystalliser, the system is kept at the initial temperature for half an hour. During the whole crystallisation experiment, stirrer speed is set to 400 rpm.

3. Crossing the Solubility Point & Seeding

After half an hour of keeping the solution at ~75° C., the cooling cycle is started. The crystalliser is cooled down to 69-71° C. This temperature depends on the solubility temperature which is determined by the sample composition. The exact temperature is determined in such a way that the solubility line is crossed for ~1° C. This brings the crystallising solution into a supersaturated state. When the supersaturated state is achieved, the solution is seeded with 1 wt. % (3.5-4 g) of finely mashed bisphenol A adduct crystals, and it is kept at the same temperature for 30 minutes.

4. Cooling to the End Crystallisation Temperature

System is cooled with the cooling rate of greater than or equal to (>) 0.2° C./min to the end crystallisation temperature of 50-60° C.

5. Filtration of the Crystal Slurry, Washing and HPLC Analysis

When the crystallisation is finished, the crystal slurry is collected in the pressure filter unit. This unit is kept at the same temperature as the end crystallisation temperature. The filtration is carried out at 0.05 bar over pressure. Washing is performed with pure phenol at 60-70° C. The total amount of washing phenol is such that the washing ratio is the same for all the experiments.

Following the above crystallisation protocol, it was determined that the final bisphenol A adduct phenol free purity linearly depends on the total impurity content in the crystallisation solution, and that greater than (>) 99.90 wt. % p,p-bisphenol A purity is achieved if the total impurity content is decreased to 50 wt. % or less from the original amount. Table 2 shows the results of different experiments where the different bisphenol A crystal impurities are achieved by using crystallisation solutions with different total impurity content. Table 2 shows crystallisation solution compositions (inlet), and achieved bisphenol A purities with impurity compositions (outlet).

The experiments prove that the bisphenol A crystal purity higher than 99.90 wt. % can be achieved. The highest impurity content, which still produced ≥99.90 wt. % bisphenol A crystal purity, was around 50 wt. % of the original impurity content which is from 8-11 wt. %. FIG. 1 shows the results of the experiments, in form of total impurity wt. % versus achieved bisphenol A purity.

Set forth below are some embodiments of the methods disclosed herein.

Embodiment 1

A method for the manufacture of bisphenol A comprising: a) reacting phenol and acetone in the presence of an acidic catalyst to form a reaction product comprising an initial concentration of bisphenol A and an initial concentration of impurities; b) diluting the reaction product with phenol, water and/or acetone, so as to decrease the impurity concentration to 50% or less of the initial concentration of impurities, and adding bisphenol A to increase the concentration thereof in the reaction product; and thereafter c) crystallising a bisphenol A/phenol adduct from the reaction product to produce a crystallised bisphenol A product.

Embodiment 2

The method according to Embodiment 1, wherein the addition of bisphenol A in step b) is such that the concentration of bisphenol A is set to 70-200% of the initial concentration of bisphenol A, preferably 75-150%, more preferably 80-125%, and most preferably, 90-110%.

TABLE 1

| | Batch # | | | | | | |
|---|---|---|---|---|---|---|---|
| | 1 wt. % | 2 wt. % | 3 wt. % | 4 wt. % | 5 wt. % | 6 wt. % | 7 wt. % |
| p,p-BPA | 24.13 | 25.32 | 25.40 | 25.35 | 25.72 | 25.06 | 24.57 |
| water | 1.4 | 1.3 | 1.30 | 1.50 | 1.40 | 1.40 | 1.40 |
| acetone | 0.15 | 0.1 | 0.10 | 0.20 | 0.17 | 0.16 | 0.15 |
| o,p-BPA | 3.03 | 3.28 | 3.39 | 3.07 | 3.05 | 3.11 | 3.13 |
| dimers | 1.27 | 1.16 | 1.18 | 1.13 | 1.08 | 1.36 | 1.20 |
| BPX-1 | 0.94 | 1.05 | 1.20 | 0.99 | 0.96 | 1.01 | 1.00 |
| Chr-1 | 0.31 | 0.39 | 0.57 | 0.47 | 0.47 | 0.51 | 0.51 |
| Spi | 0.08 | 0.07 | 0.07 | 0.06 | 0.06 | 0.08 | 0.07 |
| BPX-2 | 0.35 | 0.41 | 0.59 | 0.44 | 0.44 | 0.45 | 0.46 |
| DMX | 0.15 | 0.14 | 0.14 | 0.12 | 0.12 | 0.16 | 0.14 |
| unknown | 2.24 | 2.34 | 2.56 | 2.19 | 2.19 | 2.53 | 2.30 |
| Total impurities | 8.36 | 8.84 | 9.69 | 8.47 | 8.37 | 9.21 | 8.81 |

TABLE 2

| INLET | | | | | | | | | |
|---|---|---|---|---|---|---|---|---|---|
| Batch Rx Effl | Total Imp. [wt. %] | o,p-BPA [ppm] | dimers [ppm] | BPX-1 [ppm] | Chr-1 [ppm] | Spi [ppm] | BPX-2 [ppm] | DMX [ppm] | Unknown [ppm] |
| 7 | 8.81 | 3.13 | 1.20 | 1.00 | 0.51 | 0.07 | 0.46 | 0.14 | 2.30 |
| Dilution to | | | | | | | | | |
| 50% | 4.41 | 1.57 | 0.60 | 0.50 | 0.25 | 0.04 | 0.23 | 0.07 | 1.15 |
| 33% | 2.91 | 1.03 | 0.40 | 0.33 | 0.17 | 0.02 | 0.15 | 0.04 | 0.76 |
| 25% | 2.20 | 0.78 | 0.30 | 0.25 | 0.13 | 0.02 | 0.11 | 0.03 | 0.58 |

| Crystallisation experiments-short cooling profile OUTLET | | | | | | | | | | |
|---|---|---|---|---|---|---|---|---|---|---|
| Batch Rx Effl | Total Imp. [wt. %] | o,p-BPA [ppm] | dimers [ppm] | BPX-1 [ppm] | Chr-1 [ppm] | Spi [ppm] | BPX-2 [ppm] | DMX [ppm] | Unknown [ppm] | Purity [wt. %] |
| 7 | 8.81 | 3.134 | 1.198 | 1.004 | 0.508 | 0.073 | 0.457 | 0.136 | 2.3 | |
| Dilution to | | | | | | | | | | |
| 50% | 0.086 | 0.039 | 0.009 | 0.01 | 0.002 | 0 | 0.011 | 0 | 0.017 | 99.91 |
| 33% | 0.067 | 0.031 | 0.003 | 0.007 | 0.002 | 0 | 0.009 | 0 | 0.006 | 99.93 |
| 25% | 0.057 | 0.024 | 0.003 | 0.006 | 0.002 | 0 | 0.009 | 0 | 0.008 | 99.94 | ppm is parts per million by weight.

Embodiment 3

Method according to Embodiment 1 or 2, wherein said impurities comprise one or more from: o,p-bisphenol A, (2,4-bis(α,α-dimethyl-4-hydroxybenzyl)phenol), (4'-hydroxyphenyl-2,2,4-trimethyl chroman), (2,2',3,3'-tetrahydro-1,1'-spirobi[indene], (4-(2-(4-(4-hydroxyphenyl)-2,2,4-trimethylchroman-6-yl)propan-2-yl)phenol), (9,9-dimethylxanthene), 4-(4"-hydroxyphenyl)-2,2,4-trimethylchroman, and 2-(4'-hydroxyphenyl)-2,4,4-trimethylchroman; preferably one or more selected from the group consisting of o,p-bisphenol A, (2,4-bis(α,α-dimethyl-4-hydroxybenzyl)phenol), (4'-hydroxyphenyl-2,2,4-trimethyl chroman), (2,2',3,3'-tetrahydro-1,1'-spirobi[indene], (4-(2-(4-(4-hydroxyphenyl)-2,2,4-trimethylchroman-6-yl) propan-2-yl)phenol), (9,9-dimethylxanthene), 4-(4"-hydroxyphenyl)-2,2,4-trimethylchroman, and 2-(4"-hydroxyphenyl)-2,4,4-trimethylchroman.

Embodiment 4

Method according to any one of the preceding embodiments, wherein said initial concentration of impurities is 5-15% by total weight of the reaction product, preferably 6-12% by total weight of the reaction product or less, more preferably 7-10% by total weight of the reaction product.

Embodiment 5

Method according to any one of the preceding embodiments, wherein the concentration of p,p-bisphenol A after step b) 18-32% by total weight of the reaction product, such as 20-30%, or 22, 28%.

Embodiment 6

Method according to any one of the preceding embodiments 5, wherein step b) further comprises adding acetone to increase the concentration thereof in the reaction product.

Embodiment 7

Method according to any one of the preceding embodiments, wherein step b) further comprises adding water to increase the concentration thereof in the reaction product.

Embodiment 8

Method according to any one of the preceding embodiments, wherein the weight ratio of phenol to bisphenol A in the reaction product prior to step b) is 70-200% of the weight ratio of phenol to bisphenol A in the reaction product after step b), preferably 75-150%, more preferably 80-125%, and most preferably 90-110%; the weight ratio of acetone to bisphenol A in the reaction product prior to step b) is 70-200% of the weight ratio of acetone to bisphenol A in the reaction product after step b), preferably 75-150%, more preferably 80-125%, and most preferably 90-110%; and/or the weight ratio of water to bisphenol A in the reaction product prior to step b) is 70-200% of the weight ratio of water to bisphenol A in the reaction product after step b), preferably 75-150%, more preferably 80-125%, and most preferably 90-110%.

Embodiment 9

Method according to any one of the preceding embodiments, wherein the impurity concentration is decreased to 45% or less of the initial concentration of impurities, such as 40% or less, or 20-35%.

Embodiment 10

Method according to any one of the preceding embodiments, wherein said crystallised bisphenol A adduct product comprises 99.8% or more by total weight of p,p-bisphenol A on phenol free basis, preferably 99.9% or more, more preferably 99.92% or more on phenol free basis.

Embodiment 11

Method according to any one of the preceding embodiments, wherein said reaction product of step a) comprises: 10-50% by total weight of the reaction product of bisphenol A, preferably 15-40%; 60-85% by total weight of the reaction product of phenol; 0-5% by total weight of the reaction product of water, preferably 0-3%; 0-2% by total weight of the reaction product of acetone, preferably 0-1.5%; and 0-20% by total weight of the reaction product of by-products, preferably 2-16%.

Embodiment 12

Method according to any one of the preceding embodiments, wherein said crystallisation is carried out in a single step.

Embodiment 13

Method according to any one of the preceding embodiments, wherein said crystallising is carried out at a temperature of 40-70° C., preferably 45-65° C., more preferably 50-60° C.

Embodiment 14

Method according to any one of the preceding embodiments, wherein the initial concentration of impurities is up to 12% by total weight of the reaction product, preferably greater than zero up to 12% by total weight of the reaction product, or preferably 4 to 12% by total weight of the reaction product, or preferably 5 to 10% by total weight of the reaction product.

Embodiment 15

Bisphenol A/phenol adduct crystals obtained by the method according to any one or more of the preceding embodiments, wherein said bisphenol A has a purity of at least 99.90%, such as at least 99.92%.

Embodiment 16

Bisphenol A/phenol adduct crystals of Embodiment 15 wherein the crystallisation is carried out in a single step.

The invention claimed is:

1. A method for the manufacture of bisphenol A comprising:
   a) reacting phenol and acetone in the presence of an acidic catalyst to form a reaction product comprising an initial concentration of bisphenol A and an initial concentration of impurities;
   b) diluting the reaction product with phenol, water and/or acetone, so as to decrease the impurity concentration to 50% or less of the initial concentration of impurities, and adding bisphenol A to increase the concentration thereof in the reaction product; and thereafter
   c) crystallising a bisphenol A/phenol adduct from the reaction product to produce a crystallised bisphenol A product; wherein the addition of bisphenol A in step b) is such that the concentration of bisphenol A is set to 70-200% of the initial concentration of bisphenol A;
   and said crystallisation is carried out in a single step.

2. The method according to claim 1, wherein said impurities comprise at least one of o,p-bisphenol A, (2,4-bis(α,α-dimethyl-4-hydroxybenzyl)phenol), (4'-hydroxyphenyl-2,2,4-trimethyl chroman), (2,2',3,3'-tetrahydro-1,1'-spirobi[indene]), (4-(2-(4-(4-hydroxyphenyl)-2,2,4-trimethylchroman-6-yl)propan-2-yl)phenol), (9,9-dimethylxanthene), 4-(4'-hydroxyphenyl)-2,2,4-trimethylchroman, and 2-(4'-hydroxyphenyl)-2,4,4-trimethylchroman.

3. The method according to claim 1, wherein said initial concentration of impurities is 5-15% by total weight of the reaction product, by total weight of the reaction product.

4. The method according to claim 1, wherein the concentration of p,p-bisphenol A after step b) is 18-32% by total weight of the reaction product.

5. The method according to claim 1, wherein step b) further comprises adding acetone to increase the concentration thereof in the reaction product.

6. The method according to claim 1, wherein step b) further comprises adding water to increase the concentration thereof in the reaction product.

7. The method according to claim 1, wherein
   the weight ratio of phenol to bisphenol A in the reaction product prior to step b) is 70-200% of the weight ratio of phenol to bisphenol A in the reaction product after step b);
   the weight ratio of acetone to bisphenol A in the reaction product prior to step b) is 70-200% of the weight ratio of acetone to bisphenol A in the reaction product after step b); and/or
   the weight ratio of water to bisphenol A in the reaction product prior to step b) is 70-200% of the weight ratio of water to bisphenol A in the reaction product after step b).

8. The method according to claim 1, wherein the impurity concentration is decreased to 45% or less of the initial concentration of impurities.

9. The method according to claim 1, wherein said crystallised bisphenol A adduct product comprises 99.8% or more by total weight of p,p-bisphenol A on phenol free basis.

10. The method according to claim 1, wherein said reaction product of step a) comprises
    10-50% by total weight of the reaction product of bisphenol A;
    60-85% by total weight of the reaction product of phenol;
    0-5% by total weight of the reaction product of water;
    0-2% by total weight of the reaction product of acetone; and
    0-20% by total weight of the reaction product by-products.

11. The method according to claim 1, wherein said crystallising is carried out at a temperature of 40-70° C.

12. The method according to claim 11, wherein said crystallising is carried out at a temperature of 45-65° C.

13. The method according to claim 3, wherein said initial concentration of impurities is 6-12% by total weight of the reaction product.

14. The method according to claim 4, wherein the concentration of p,p-bisphenol A after step b) is 20-30% by total weight of the reaction product.

15. The method according to claim 7, wherein
    the weight ratio of phenol to bisphenol A in the reaction product prior to step b) is 75-150% of the weight ratio of phenol to bisphenol A in the reaction product after step b);
    the weight ratio of acetone to bisphenol A in the reaction product prior to step b) is 75-150% of the weight ratio of acetone to bisphenol A in the reaction product after step b); and/or
    the weight ratio of water to bisphenol A in the reaction product prior to step b) is 75-150% of the weight ratio of water to bisphenol A in the reaction product after step b).

16. The method according to claim 15, wherein
    the weight ratio of phenol to bisphenol A in the reaction product prior to step b) is 80-125% of the weight ratio of phenol to bisphenol A in the reaction product after step b);
    the weight ratio of acetone to bisphenol A in the reaction product prior to step b) is 80-125% of the weight ratio of acetone to bisphenol A in the reaction product after step b); and/or
    the weight ratio of water to bisphenol A in the reaction product prior to step b) is 80-125% of the weight ratio of water to bisphenol A in the reaction product after step b).

17. The method according to claim 8, wherein the impurity concentration is decreased to 20-35% of the initial concentration of impurities.

18. The method according to claim 10, wherein said reaction product of step a) comprises
    15-40% by total weight of the reaction product of bisphenol A;
    0-3% by total weight of the reaction product of water;
    0-1.5% by total weight of the reaction product of acetone; and
    2-16% by total weight of the reaction product of by-products.

* * * * *